United States Patent [19]

Wright et al.

[11] 4,121,036
[45] Oct. 17, 1978

[54] 3-AMINO-2-HYDRAZINOPYRIDINE DERIVATIVES

[75] Inventors: George C. Wright, Norwich; James L. Butterfield, New Berlin, both of N.Y.

[73] Assignee: Morton-Norwich Products, Inc., Norwich, N.Y.

[21] Appl. No.: 770,581

[22] Filed: Feb. 22, 1977

[51] Int. Cl.$^2$ .................... C07D 213/77; A61K 31/44
[52] U.S. Cl. ................................ 542/417; 260/296 R; 424/263
[58] Field of Search .................... 542/417; 260/296 R, 260/240 G

[56] References Cited

PUBLICATIONS

Bernstein, et al., J. Amer. Chem. Soc., 69, pp. 1151–1158, (1947).
Sommer, L., Chem. Abstracts, vol. 79, No. 19–21, 1973, parag. 121493(c).
Bell, et al., Chem. Abstracts, vol. 70, 1969, parag. 87484(c).

*Primary Examiner*—Henry R. Jiles
*Assistant Examiner*—Cary Owens
*Attorney, Agent, or Firm*—Anthony J. Franze

[57] ABSTRACT

Schiff base derivatives of 3-amino-2-hydrazinopyridine are useful as antihypertensive agents.

4 Claims, No Drawings

3-AMINO-2-HYDRAZINOPYRIDINE DERIVATIVES

This invention is concerned with chemical compounds. In particular, it is concerned with chemical compounds of the formula:

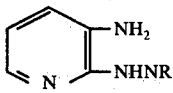

wherein R is 3,4-dimethoxybenzylidene, 4-hydroxybenzylidene or isopropylidene and their hydrochloride salts.

The compounds of this invention possess pharmacological activity. They are capable when administered to hypertensive animals in less than toxic dose of reducing arterial blood pressure. The antihypertensive ability of the compounds of this invention is demonstrated by their intraperitoneal administration in a dose of about 50 mg/kg dispersed in distilled water to unanesthetized, spontaneously hypertensive rats whereupon arterial blood pressure is reduced.

The compounds of this invention are readily formulated in conventional pharmaceutical dosage forms such as tablets, elixirs, suspensions, capsules and the like employing known excipients and adjuvants.

In order that this invention may be readily available to and understood by those skilled in the art the following illustrative examples are supplied.

EXAMPLE I

Veratraldehyde 3-Amino-2-pyridylhydrazone Hydrochloride

A. Veratraldehyde 3-Nitro-2-pyridylhydrazone Hydrochloride

To a mixture of the hemi-hydrochloride of 2-hydrazino-3-nitropyridine (24 g, 0.14 mole) and $H_2O$ (140 ml) was added veratraldehyde (23 g, 0.14 mole) in ethanol (150 ml) with hand stirring over 10 min. The mixture was stored in the refrigerator overnight and the product was collected by filtration and washed with ethanol (3 × 10 ml), ether, yield: 35 g. The product (20 g ) was heated (steam bath) with a solution of 90% MeOH (10% HCl) (800 ml) and filtered to collect the insoluble product (1). The filtrate was cooled in the refrigerator overnight and the resultant product (2) was collected; m.p. 199°–203°, yield: 9.6 g. Product 1. was recrystallized from filtrate (2.); m.p. 195°–200°, yield, 10.3 g. Total yield: 19.9 g (42%).

Anal. Calcd. as $C_{14}H_{14}N_4O_4.HCl$: C, 49.64; H, 4.46; N, 16.54.

Found: C, 49.98; H, 4.61; N, 16.86.

B. A mixture of the free base A (30 g, 0.010 mole), MeOH (700 ml), and 5% Pd/C (50% $H_2O$) (3.0 g) was subjected to hydrogenation. A pressure drop of 88% of theory was observed. The reaction mixture was treated with Darco at room temperature, filtered of catalyst, concentrated under reduced pressure to a volume of 200 ml, and stored in the refrigerator for 3 hours. The product (free base) was collected and washed with cold MeOH (2 × 10 ml), EtOH (4 × 10 ml), iPrOH (3 × 10 ml), ether; m.p. 146°–148°, yield: 17 g (55%).

Treatment of the product (free base) (15 g) in MeOH (150 ml) in the cold, with a solution of dry HCl in iPrOH (10 ml) to a pH 2, gave the hydrochloride.

Recrystallization of the hydrochloride (18 g) from MeOH (425 ml) gave the product; m.p. 213°–217°, yield: 10 g (37%).

Anal. Calcd. as $C_{14}H_{16}N_4O_2.HCl$: C, 54.46; H, 5.55; N, 18.15.

Found: C, 54.37; H, 5.69; N, 18.01.

EXAMPLE II

Acetone 3-Amino-2-pyridylhydrazone Hydrochloride

A. Acetone 3-Nitro-2-pyridylhydrazone

A mixture of the hemi-hydrochloride of 2-hydrazino-3-nitropyridine and ethanol (105 ml) was treated with acetone (70 ml) with hand stirring. The mixture was heated (steam bath) for 10 min., stored at room temperature for 1 hour and in the refrigerator for 2 hrs, and the resultant product was collected by filtration and washed with cold isopropanol; m.p. 126°–128°, yield: 32 g (55%).

An analytical sample was prepared by recrystallization from acetone, m.p. 125°–127°.

Anal. Calcd. as $C_8H_{10}N_4O_2$: C, 49.48; H, 5.19; N, 28.88.

Found: C, 49.46; H, 5.25; N, 28.70.

A solution of A (24.8 g, 0.13 mole) in methanol (400 ml), treated with a solution of dry HCl (isopropanol) (11 ml) to a pH of 3 and 5% Pd/C (50% $H_2O$) (2.4 g) was subjected to hydrogenation. A pressure drop of 92% of theory was observed. The reaction mixture was Darcoed, filtered, neutralized with a solution of dry HCl (isopropanol) to a pH of 6–7 with cooling, and concentrated under reduced pressure to a volume of ca. 35 ml. The residue was treated with acetone (100 ml) and stored in the refrigerator over the weekend; the resultant product was collected by filtration and washed well with cold isopropanol; m.p. 162°–165°, yield: 9.0 g (34%).

An analytical sample was prepared by twice recrystalling from absolute ethanol, m.p. 165°–168°.

Anal. Calcd. as $C_8H_{12}N_4.HCl$: C, 47.88; H, 6.53; N, 27.52.

Found: C, 47.63; H, 6.53; N, 27.57.

EXAMPLE III p-Hydroxybenzaldehyde 3-Amino-2-pyridylhydrazone Hydrochloride

A. To a mixture of the hemi-hydrochloride of 2-hydrazino-3-nitropyridine (25. 8 g, 0.15 mole) and water (90 ml) was added a solution of p-hydroxybenzaldehyde (18.3 g, 0.15 mole) in ethanol (144 ml) with hand stirring over 10 min. The mixture was stored at room temperature for 2 hours and the product was collected by filtration and washed with cold ethanol (4 × 10 ml), ether; yield: 32 g (83%) of p-hydroxybenzaldehyde 3-nitro-2-pyridylhydrazone.

B. A mixture of p-hydroxybenzaldehyde 3-nitro-2-pyridylhydrazone (32 g, 0.12 mole), methanol (800 ml), and 5% Pd/C (50% $H_2O$) (3.2 g) was subjected to hydrogenation. A pressure drop of 102% of theory was observed in 3 hours. The reaction mixture was filtered to collect the product-catalyst mixture and washed well with methanol. The crude product was treated with a mixture of methanol (100 ml) and isopropanol (60 ml), and then treated with a solution of HCl-isopropanol to a pH of 4–5, cooling in an ice bath. The product was collected by filtration and washed well with isopropanol, then ether. Recrystallization from 97.5% methanol (water) gave the product; yield: 10 g (31%).

A second recrystallization from the same solvent gave an analytical sample, m.p. 237°–239°.

Anal. Calcd. as $C_{12}H_{12}N_4 \cdot HCl$: C, 54.44; H, 4.95; N, 21.17.

Found: C, 54.43; H, 4.97; N, 21.24.

What is claimed is:

1. A compound of the formula:

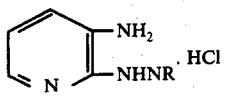

wherein R is 3,4-dimethoxybenzylidene, 4-hydroxybenzylidene or isopropylidene.

2. Veratraldehyde 3-amino-2-pyridylhydrazone hydrochloride.

3. Acetone 3-amino-2-pyridylhydrazone hydrochloride.

4. 4-Hydroxybenzaldehyde 3-amino-2-pyridylhydrazone hydrochloride.

* * * * *